US007618806B2

(12) United States Patent
Reilly et al.

(10) Patent No.: US 7,618,806 B2
(45) Date of Patent: Nov. 17, 2009

(54) METHODS AND APPARATUS FOR MASS SPECTRAL ANALYSIS OF PEPTIDES AND PROTEINS

(75) Inventors: James P. Reilly, Bloomington, IN (US); Matthew S. Thompson, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 380 days.

(21) Appl. No.: 10/578,679

(22) PCT Filed: Nov. 15, 2004

(86) PCT No.: PCT/US2004/041171

§ 371 (c)(1), (2), (4) Date: May 9, 2006

(87) PCT Pub. No.: WO2005/050172

PCT Pub. Date: Jun. 2, 2005

(65) Prior Publication Data

US 2007/0085040 A1 Apr. 19, 2007

Related U.S. Application Data

(60) Provisional application No. 60/519,991, filed on Nov. 14, 2003.

(51) Int. Cl.
*C12M 1/00* (2006.01)

(52) U.S. Cl. .................................................. 435/283.1

(58) Field of Classification Search ................. 250/288, 250/425, 423 P; 96/16
See application file for complete search history.

(56) References Cited

U.S. PATENT DOCUMENTS

| | | | |
|---|---|---|---|
| 4,920,264 | A | 4/1990 | Becker |
| 6,323,482 | B1 | 11/2001 | Clemmer et al. |
| 2003/0189171 | A1 | 10/2003 | Londry et al. |

OTHER PUBLICATIONS

Butcher et al. "Vacuum Ultraviolet Radiation for Single-Photoionization Mass Spectrometry: A Review", Microchemical Journal, 1999, 62:354-362.*

Muhlberger et al. "Single Photon Ionization (SPI) via Incoherent VUV-Excimer Light: Robust and Compact Time-of-Flight Mass Spectrometer for On-line, Real-Time Process Gas Analysis". Anal. Chem. 2002, 74:3790-3801.*

Baldwin et al. "Matrix-Assisted Laser Desorption/Ionization coupled with Quadrupole/Orthogonal Acceletation Time-of-Flight Mass Spectrometry for Protein Discovery, Identification, and structural anlysis", Anal. Chem. 2001, 73:1707-1720.*

PCT International Search Report for PCT/US2004/041171completed by the US Searching Authority on Sep. 26, 2005.

Barbacci, D. C., et al., "Sequence and Side-Chain Specific Photofragment (193 nm) Ions from Protonated Substance P by Matrix-Assisted Laser Desorption Ionization Time-of-Flight Mass Spectrometry," *J. Am. Soc. Mass Spectrom.* 10: 1038-1040 (1999).

Beardsley, R. L., and Reilly, J. P., "Quantitation Using Enhanced Signal Tags: A Technique for Comparative Proteomics," *J Proteome Research* 2:15-21 (2003).

Beardsley, R. L., et al., "Optimization of Guanidination Procedures for Maldi Mass Mapping," *Anal. Chem.* 74, 1884-1890 (2002).

Bowers, W. D., et al. "Fragmentation of Oligopeptide Ions Using Ultraviolet Laser Radiation and Fourier Transform Mass Spectrometry," *J. Am. Chem. Soc.*, 106: 7288-7289 (1984).

Breci, L. A., et al., "Cleavage N-Terminal to Proline: Analysis of a Database of Peptide Tandem Mass Spectra," *Anal. Chem.*, 75,1963-1971 (2003).

Cooper, H. J., et al., "Characterization of Amino Acid Side Chain Losses in Electron Capture Dissociation," *J Amer Soc Mass Spectrom*, 13, 241-249 (2002).

Harrison, A. G. "The Gas-Phase Basicities and Proton Affinities of Amino Acids and Peptides," *Mass Spectrom Reviews*, 16, 201-217 (1997).

Hunt, D. F., et al., "Protein Sequencing by Tandem Mass Spectrometry," *Proc. Natl. Acad. Sci. USA* 83, 6233 -6237 (1986).

Hunt, D. F., et al., "Sequence Analysis of Oligopeptides by Secondary Ion/Collision Activated Dissociation Mass Spectrometry", *Anal. Chem.*, 53, No. 11, 1704-1706 (1981).

Johnson, R. S., et al., "Collision-Induced Fragmentation of $(M+H)^+$Ions of Peptides. Side Chain Specific Sequence Ions*" *Int. J. Mass Spectrom Ion Processes* 86:137-154 (1988).

Kaufmann, R., et al., "Sequencing of peptides in a time-of-flight mass spectrometer: evaluation of postsource decay following matrix-assisted laser desorption ionisation (MALDI)," *Int. J. Mass Spectrom. and Ion Proc.* 131: 355-385 (1994).

Kelleher, N. L., et al., "Top Down versus Bottom Up Protein Characterization by Tandem High-Resolution Mass Spectrometry," *J. Am. Chem. Soc.* 121, No. 4, 806-812 (1999).

Keough, T., et al., "A method for high-sensitivity peptide sequencing using postsource decay matrix-assisted laser desorption ionization mass spectrometry," *Proc. Natl. Acad. Sci. USA* 96, 7131-7136 (1999).

Kruger, N. A., et al., "Electron capture versus energetic dissociation of protein ions," *Int. J. Mass Spectrom.*, 182/183, 1-5(1999).

(Continued)

*Primary Examiner*—Karen Cochrane Carlson
*Assistant Examiner*—Bin Shen
(74) *Attorney, Agent, or Firm*—Barnes & Thornburg LLP

(57) ABSTRACT

Apparatus, device, and methods for fragmenting high molecular weight molecular ions, such as peptides or proteins, by treating the ions with predetermined wavelengths of light are described. Vacuum ultraviolet radiation as a source of predetermined wavelengths of laser light is described in one embodiment. A device (50) is described having a sample, such as a peptide, protein, protein digest, and the like enters through inlet (55) and is irradiated with a first source of light (60), which illustratively may be a laser light. The first source of laser light is illustratively at a wavelength and energy sufficient to convert molecules in the sample into molecular or precursor ions.

10 Claims, 6 Drawing Sheets

OTHER PUBLICATIONS

Little, D. P., et al., "Infrared Multiphoton Dissociation of Large Multiply Charged Ions for Biomolecule Sequencing," *Anal. Chem.*, 66, No. 18, 2809-2815(1994).

Martin, S. A., et al., "Photon-Induced Dissociation with a Four-Sector Tandem Mass Spectrometer," *J. Am. Soc. Mass. Spectrom.*, 1, 107-109 (1990).

Medzihradszky, K. F., et al., "The Characteristics of Peptide Collision-Induced Dissociation Using a High-Performance MALDI-TOF/TOF Tandem Mass Spectrometer, "*Anal. Chem.*, 72, 552-558 (2000).

Peterson, D. L., et al., "Polarized Electronic Absorption Spectrum of Amides with Assignments of Transitions," *J. Am. Chem. Soc.*, 79, 2375-2382 (1957).

Preiss, J. W., et al. "Spectra of Some Amino Acids, Peptides, Nucleic Acids, and Protein in the Vacuum Ultraviolet",*J. Chem. Phys.*, 25, No. 1, 138-141 (1956).

Price, W. D., et al. "Tandem Mass Spectrometry of Large Biomolecule Ions by Blackbody Infrared Radiative Dissociation," *Anal. Chem.*, 68, No. 5, 859-866 (1996).

Roepstorff, P. et al., "Proposal for a Common Nomenclature for Sequence Ions in Mass Spectra of Peptides," *Biomed. Mass Spectrom.*, 11, No. 11, 601 (1964).

Spengler, B., et al., "Fundamental Aspects of Postsource Decay in Matrix-Assisted Laser Desorption Mass Spectrometry. 1. Residual Gas Effects," *J. Phys. Chem.*, 96, No. 24, 9678-6984 (1992).

Williams, E. R., et al., "Surface-Induced Dissociation of Peptide Ions in Fourier-Transform Mass Spectrometry," *J Am Soc Mass Spectrom*, 1, 413-416 (1990).

Zimmerman, J. A., et al. "Muttiphoton Ionization of Laser-Desorbed Neutral Molecules in a Fourier Transform Ion Cyclotron Resonance Mass Spectrometer," *Anal. Chem.*, 63, 361-365(1991).

Zubarev, R. A., et al., "Electron Capture Dissociation Of Multiply Charged Protein Cations. A Nonergodic Process," *J. Am. Chem. Soc.*, 120, 3265-3266 (1998).

* cited by examiner

METHODS AND APPARATUS FOR MASS SPECTRAL ANALYSIS OF PEPTIDES AND PROTEINS

CROSS REFERENCE TO RELATED APPLICATIONS

This application is a U.S. national counterpart application, filed under 35 U.S.C. § 371, of international application serial No. PCT/US2004/041171 filed Nov. 15, 2004, which claims priority to U.S. Provisional Patent Application No. 60/519,991 entitled "Methods And Apparatus For Mass Spectral Analysis Of Peptides And Proteins" which was filed on Nov. 14, 2003. The entireties of the disclosures of which are hereby incorporated by reference.

GOVERNMENT RIGHTS

This invention was made in whole or in part with support from The National Institutes of Health through NIH Grant No. GM061336. The United States Government may have certain rights in this invention.

TECHNICAL FIELD

This invention relates generally to the analysis of molecules by mass spectrometry and, more specifically to the analysis of peptides and proteins by fragmentation and mass spectrometry.

BACKGROUND

Mass spectrometry techniques have been used to produce sequence information by fragmenting peptide ions. One conventional method is collision-induced dissociation. However, with this method, multiple fragment types are often produced (mostly b and y type), the sequence coverage may vary widely, and the observed fragmentation often cannot be readily predicted from the peptide sequence. For example, Scheme 1 shows (a) the standard nomenclature for peptide fragmentation, and (b) products of hemolytic radical cleavage of an example peptide; however, the location of the added proton is not specified.

Scheme 1

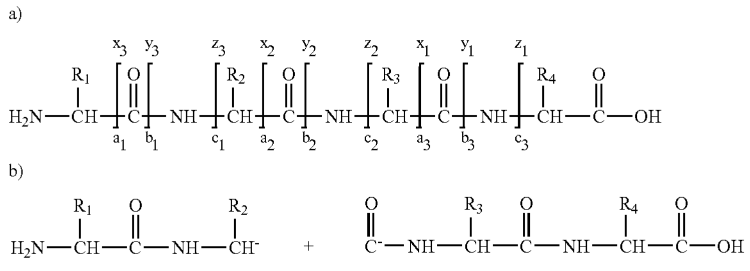

Therefore, identification is generally made by comparing measured data with theoretical data from a database of known protein sequences, and successful identifications usually rely on the availability of such databases. However, database errors, sample mutations, and the presence of post-translationally modified peptides or proteins in the sample may reduce the likelihood of identifying those peptides and proteins.

Another ion fragmentation or activation method, electron capture dissociation (ECD), is believed to involve the capture of an electron by a multiply-charged protein ion leading to the formation of a hydrogen atom that subsequently induces cleavage between the backbone nitrogen and α-carbon. See, e.g., R. A. Zubarev, N. L. Kelleher, F. W. McLafferty, *J. Am. Chem. Soc.* 120:3265 (1998); N. A. Kruger et al., *Int. J. Mass Spectrom.* 182/183:1 (1999). ECD is capable of inducing localized excitation; however, dissociation should subsequently occur before the internal energy is randomized. It has been observed that c and z type fragment ions are generated rather than the typical b and y type fragment ions. This ECD phenomenon has been used in the sequencing and identification of protein ions in specialized mass spectrometers. See, e.g., N. L. Kelleher et al., *J. Am. Chem. Soc.* 121:806 (1999). However, ECD cannot be used in many mass spectrometers because they contain electric fields that manipulate and control the movement of the ionized sample and sample fragments. Those fields interfere with the introduction of the electron beams that are necessary for ECD.

Bond-selective chemistry has been a subject of research by photochemists since the development and availability of tunable laser light sources. However, such bond-selective chemistry has not been applied to relatively large molecular systems or molecular systems having relatively high molecular weights, such as peptides and proteins, in part because rapid intramolecular vibrational relaxation appears to redistribute energy throughout large and/or high molecular weight molecules and their molecular ions on timescales faster than the dissociation needed for the analyses. Thus, the bond-breaking selectivity that is desired by using bond-selective chemistry in such an excitation process is often lost.

Other conventional methods for peptide ion fragmentation use an array of different activation methods, such as blackbody radiation, infra red (IR) multiphoton excitation, UV laser excitation, and collisions with gas phase molecules or surfaces. See, e.g., W. D. Price, P. D. Schnier, E. R. Williams, *Anal. Chem.* 68:859 (1996); J. A. Zimmerman, C. H. Watson, J. R. Eyler, *Anal. Chem.* 63:361 (1991); D. P. Little, J. P. Speir, M. W. Senko, P. B. O'Connor, F. W. McLafferty, *Anal. Chem.* 66:2809 (1994); W. D. Bowers, S. Delbert, R. L. Hunter, R. T. McIver, *J. Am. Chem. Soc.* 106:7288 (1984); S. A. Martin, J. A. Hill, C. Kittrell, K. Biemann, *J. Am. Soc. Mass Spectrom.* 1:107 (1990); D. C. Barbacci, D. H. Russell, *J. Am. Soc. Mass Spectrom.* 10:1038 (1990); D. F. Hunt, W. M. Bone, J. Shabanowitz, J. Rhodes, J. M. Ballard, *Anal. Chem.* 53:1704 (1981); E. R. Williams, K. D. Henry, F. W. McLafferty, J. Shabanowitz, D. F. Hunt, *J. Am. Soc. Mass Spectrom.* 1:413 (1990). These activation methods involve vibrational excitation of the precursor ion; however, the resulting peptide bond cleavages tend to produce very similar types of daughter ions, generally referred to as b and y type fragments. See, P. Roepstorff, J. Fohlman, *Biomed. Mass Spectrom.* 11:601 (1984).

Therefore, there is a need for methods and devices that are useful for fragmenting large and/or high molecular weight ions, including peptide and protein ions, that may lead to more predictable and interpretable results.

SUMMARY OF THE INVENTION

The invention described herein includes methods, devices, and apparatus for analyzing large and/or high molecular weight molecules and compounds by fragmentation of their ions. In one aspect, the fragmented ions are analyzed by mass spectrometry. Large and/or high molecular weight compounds as described herein include, but are not limited to, peptides, proteins, enzymatic digests of proteins, carbohydrates, glycopeptides, glycoproteins, nucleic acids, synthetic polymers, and the like.

In one illustrative embodiment, the large and/or high molecular weight molecules are peptides, proteins, and/or protein digests. In one aspect, the methods for analyzing such molecules by mass spectrometry include the step of initial ionization of the large and/or high molecular weight molecules followed by fragmentation of the resulting ions. In another aspect where the large and/or high molecular weight compounds are peptides and/or proteins, the fragmentation is performed in an efficient and substantially predictable manner.

In another illustrative embodiment, the methods, devices, and apparatus described herein are used to sequence unknown proteins, protein digests, and/or peptides by mass spectrometry.

In another illustrative embodiment, the methods, apparatus, and devices described herein can be included in and used in a variety of different types of mass spectrometers, including conventional mass spectrometers that may also include a variety of different types of ionization methods. Such conventional mass spectrometers may be modified or adapted to include the fragmentation devices described herein.

In another illustrative embodiment, devices and apparatus are described herein for fragmenting ions of large molecules or high molecular weight molecules, where the devices and apparatus use methods described herein. Such methods include the steps of (a) providing one or more ionized sample large molecules or ionized high molecular weight compounds in an ion trap, (b) isolating one or more particular ionized sample molecules by mass selection, and (c) treating the one or more particular ionized sample molecules with light having a predetermined wavelength and a sufficient energy to cause photodissociation. The predetermined wavelength is selected to interact with a particular bond type present in the one or more molecules. It is appreciated that such selection of a predetermined wavelength may increase the production of atypical fragment ions relative to the commonly observed b and y type fragment ions that arise from energy redistribution in large and/or high molecular weight ions.

In another embodiment, devices and apparatus are described herein that include a mass spectrometer, a source of ionized sample material, and a source of vacuum ultraviolet (VUV) radiation having a predetermined wavelength. In one aspect, the mass spectrometer may be any conventional mass spectrometer, or a mass spectrometer that has been adapted or modified with the devices and apparatus described herein. In another aspect, the source of ionized sample material may be from any conventional system capable of ionizing a sample.

In another aspect, the predetermined wavelength of vacuum ultraviolet radiation is laser light having a wavelength less than about 190 nm. In another aspect, the predetermined wavelength is within the range from about 130 nm to about 175 nm, and/or within the range from about 155 nm to about 160 nm. In another aspect, the predetermined wavelength is about 157 nm.

In another aspect where the large and/or high molecular weight molecular ions are formed from peptide and/or protein samples, the laser light having a sufficient energy is light having at least about 5 eV of energy. In another aspect, the laser light has an energy within the range from about 5 eV to about 9 eV, and/or within the range from about 7.5 eV to about 8.5 eV.

In another embodiment, methods are described herein for analyzing sample materials. Such methods include the steps of (a) ionizing the sample, (b) treating the sample in the reduced atmosphere of a mass spectrometer with light at a predetermined wavelength to cause fragmentation, and (c) measuring the mass/charge ratio of the resulting fragments. Such methods may also include any number of mass selection steps and/or mass storage steps and/or mass analysis steps using conventional components capable of accomplishing such steps.

In another embodiment, methods are described herein for fragmenting peptides and proteins at the bond connecting the α-carbon and the carbonyl carbon. The methods include the step of treating ionized large and/or high molecular weight molecular ions, including peptide and protein ions, in a mass spectrometer with radiation at a predetermined wavelength to cleave a specific bond type present in the large and/or high molecular weight ions. Illustratively, the predetermined wavelength is about 157 nm, and the bond type that is cleaved connects the α-carbon and the carbonyl carbon.

DETAILED DESCRIPTION

Figure 5:
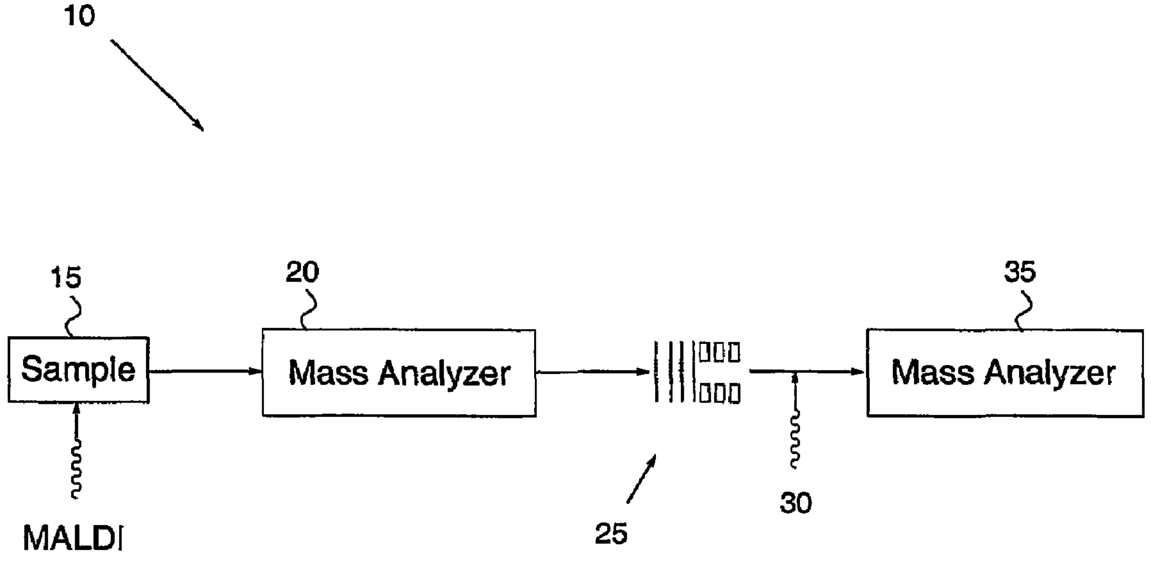
FIG. 5 shows an illustrative apparatus 10 for analyzing high molecular weight compounds by fragmentation.

In one illustrative embodiment, an apparatus 10 is described and includes the components and features shown in FIG. 5. The apparatus may be used for analyzing large molecular complexes and/or high molecular weight compounds, including peptides, proteins, enzymatic digests of proteins, carbohydrates, glycopeptides, glycoproteins, nucleic acids, synthetic polymers, and the like. Referring to FIG. 5, the apparatus may be adapted from a conventional instrument that employs collision cells (See, K. F. Medzihradsky et al., *Anal. Chem.* 72:552 (2000), the disclosure of which is incorporated herein by reference. The adaptation includes a device that causes or induces ion fragmentation using a source of vacuum ultraviolet (VUV) laser light. In one aspect, precursor or molecular ions are generated by MALDI from sample 15, and those ions are accelerated into a first mass analyzer 20. First mass analyzer 20 optionally includes an ion trap (not shown). In variations where first mass analyzer 20 is a time of flight analyzer, a linear flight tube (not shown) may also be included. In one illustrative aspect, the ions are separated in first mass analyzer 20. During this first stage, post-source decay (PSD) ions are formed by unimolecular dissociation and continue to travel with the precursor ion. See, R. Kaufmann, D. Kirsch, B. Spengler, *Int. J. Mass Spectrom. and Ion Proc.* 131:355 (1994). At the end of this first stage, one or more particular ions and/or its fragments are selected by ion gate 25 and then irradiated with a synchronized pulse of a predetermined wavelength of laser light at a predetermined energy from laser source 30.

In variations of the configuration shown in FIG. 5, ions exiting first mass analyzer 20 are sampled or selected by accelerating the ions in an orthogonal direction to the flow from first mass analyzer 20, rather than in a direction colinear or parallel to the flow from first mass analyzer 20. Therefore, ion gate 25 is oriented perpendicular to the flow through first mass analyzer 20 allowing selected ions to be selectively located for acceleration. It is appreciated that such transverse or orthogonal configurations may improve overall performance of apparatus 10, and improve resolution.

The precursor ions and fragments thereof are then reaccelerated into a second stage of the apparatus that includes a mass analyzer 35, where each is separated and detected, optionally with isotopic resolution obtained for both the parent and fragment ions. In one illustrative aspect, mass analyzer 35 is a reflectron time-of-flight mass analyzer; however, it is appreciated that other mass analyzers, including but not limited to linear time of flight (LTOF), time of flight-time of flight (TOF-TOF), reflectron time of flight, linear ion trap-time of flight (LIT-TOF), triple-quadrupole, magnetic sector, quadrupole time-of-flight (Q-TOF), Fourier transform ion cyclotron resonance mass analyzers may be used in contemplated variations of the apparatus 10. In another illustrative aspect, laser source 30 is a molecular fluorine ($F_2$) laser. In one illustrative variation, the $F_2$ laser is operated on alternating MALDI shots. In this variation, it is appreciated that the post-source decay fragments may be more easily distinguished from those generated by photodissociation by subtraction of the signals generated from alternate MALDI shots. In another variation, 2,5-dihydroxybenzoic acid (DHB) is used as a matrix for photodissociation experiments. It is further appreciated that a 2,5-dihydroxybenzoic acid (DHB) matrix may minimize the production of post-source decay fragments, as reported by B. Spengler, D. Kirsch, R. Kaufmann, in *J. Phys. Chem.* 96, 9678 (1992), the disclosure of which is incorporated herein by reference. It is understood that an α-cyano-4-hydroxycinnamic acid (CHCA) matrix may be used to deliberately generate PSD fragments. It is further understood that a CHCA matrix may also be used for photodissociation if background subtraction of PSD data is performed. It is appreciated that other matrices or additives may also be used in variations of the embodiments described herein, such as cinnamic acid analogs and derivatives like ferulic acid, sinapinic acid, and the like, hydroxypicolinic acid, and other matrices.

In another aspect, the predetermined wavelength is chosen to selectively or specifically excite particular bond types present in the molecules under analysis. In another aspect, the predetermined energy is chosen to be sufficiently high to cause selective or specific breakage of particular bond types in the molecules under analysis.

Illustratively, the molecules under analysis are peptides and/or proteins, including high molecular weight peptides and/or proteins. Illustrative wavelengths are less than about 190 nm. In variations, illustrative wavelengths are selected within the range from about 130 nm to about 175 nm, and/or within the range from about 155 nm to about 160 nm. Illustrative energies are at least about 5 eV, within the range from about 5 eV to about 9 eV, and/or within the range from about 7.5 eV to about 8.5 eV. Another illustrative energy and wavelength is about 1 mJ of about 157 nm (7.9 eV photon energy) light produced from a molecular fluorine ($F_2$) laser. However, it is to be understood that higher energy photons are also contemplated, including energies that are much greater than about 5 eV, such as about 12 eV or greater, or about 20 eV or greater.

Any of a wide variety of light sources capable of producing the predetermined wavelengths along with the predetermined energies is contemplated herein, including but not limited to laser light sources, other vacuum ultraviolet lasers, and beams of coherent light generated through nonlinear optical methods. Incoherent light produced by a synchrotron or created, for example, in electrical discharges may also be used to induce ion photodissociation in the methods, devices, and apparatus described herein. It is appreciated that light produced by a synchrotron may be at very high energy, such as light having a wavelength of about 50 nm or even less. Such high energy light is contemplated, and may be used in the methods, devices, and apparatus described herein.

Theoretical and spectroscopic studies of small polypeptides suggest that they absorb rather strongly in the vacuum ultraviolet (VUV) region of the spectrum, and the chromophore involved in the process is associated with the peptide backbone amides. See, e.g., J. W. Price, R. Setlow, *J. Chem. Phys.* 25:138 (1956). A strong band occurs near 190 nm, and this transition can be excited using 193 nm ArF laser light. See, e.g., D. L. Peterson, W. T. Simpson, *J. Am. Chem. Soc.* 79:2375 (1957). In addition, the 6.4 eV photon energy of ArF laser light is similar to that imparted in ECD. However, photodissociation experiments at this wavelength generally produce the common b and y fragments that are indicative of energy randomization. In addition, and in contrast to vibrational excitation methods, some non-specific side chain fragmentation is also observed with this method.

Figure 6:
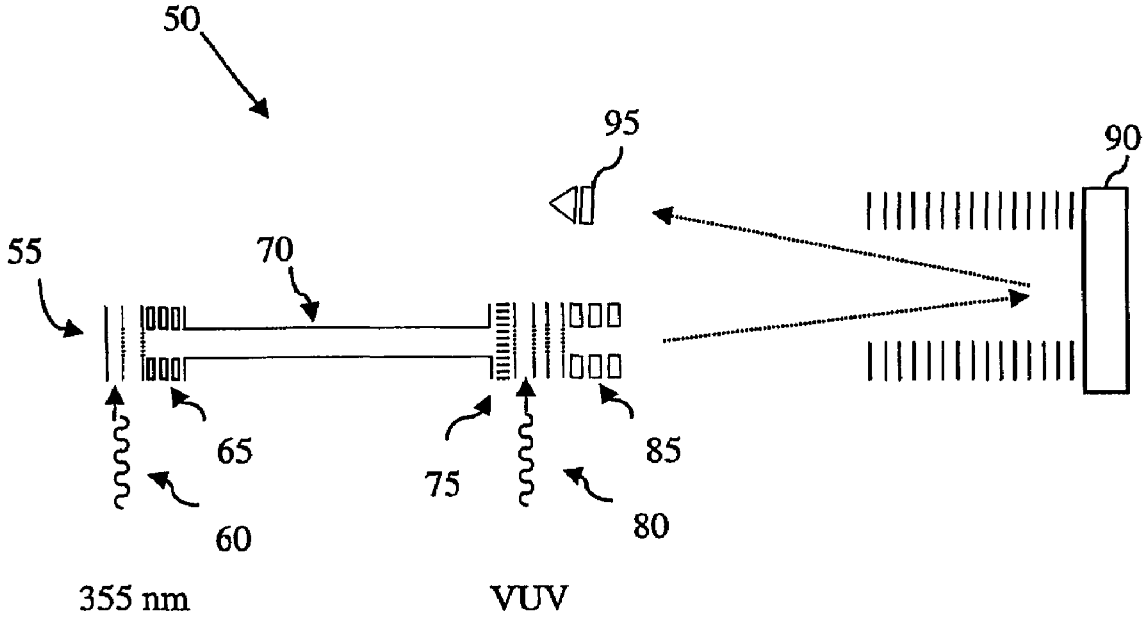
FIG. 6 shows an illustrative apparatus 50 for analyzing high molecular weight compounds by fragmentation.

In another illustrative embodiment, a device 50 representing a TOF-TOF instrument is described and includes the components and features shown in FIG. 6. Referring to FIG. 6, a sample, such as a peptide, protein, protein digest, and the like enters through inlet 55 and is irradiated with a first source of light 60, which illustratively may be laser light. The first source of laser light is illustratively at a wavelength and energy sufficient to convert molecules in the sample into molecular or precursor ions. Illustratively, the wavelength is about 355 nm. In one variation, the ions are produced from the sample using MALDI; however, other initial ionization methods may be used in variations of the device 50. The precursor or molecular ions enter focusing lens 65 coupled to linear flight tube 70. In variations of this configuration, the focusing lens is coupled to a mass selecting component, including but not limited to a quadrupole device. The mass selecting component selects certain predetermined mass values and accelerates those ion masses into linear flight tube 70. Linear flight tube 70 is coupled to ion gate 75, which allows predetermined mass values to exit ion trap 70. Those ion masses are contacted with a second source of light 80, which illustratively may be laser light, emitting radiation at a predetermined wavelength and having a sufficient energy to cause photodissociation of predetermined bonds in the ion masses leading to fragmentation. The resulting fragmented ion masses are accelerated through focusing lens 85 into a mass analyzer, such as a reflecting time of flight component 90 to detector 95.

In variations of the configuration shown in FIG. 6, the sample entering inlet 55 is ionized using another conventional component, including electrospray, sonic spray, electro-sonic spray, fast atom bombardment, and the like. It is appreciated that such ionization of the sample is advantageously performed to minimize fragmentation, in order that the primary fragmentation pattern observed is accomplished by the second source of laser light 80.

In other variations of the configuration shown in FIG. 6, ions exiting linear flight tube 70 are sampled or selected by accelerating the ions in an orthogonal direction to the flow from linear flight tube 70, rather than in a direction co-linear or parallel to the flow from linear flight tube 70. Therefore, focusing lens 85 is oriented perpendicular to the flow through linear flight tube 70 allowing selected ions to be selectively located for acceleration. It is appreciated that such transverse or orthogonal configurations may improve overall performance of apparatus 50, and improve resolution.

In another illustrative embodiment, a variation of the device 50 shown in FIG. 6 is described, and represents another homebuilt MALDI tandem time of flight instrument. Precursor ions are separated in a linear TOF apparatus, and those precursor ions of interest are selected by an ion gate. An unfocused 10-ns, 2-mJ laser pulse with a cross section of 5 mm×10 mm, and having a wavelength of about 157 nm VUV light generated from an $F_2$ laser, interacts with the selected ions. Precursor and fragment ions are then reaccelerated, separated, and detected in a reflectron TOF analyzer. Spectra with and without photodissociation are recorded on alternating shots so that the post source decay (PSD) contribution can be subtracted away. For comparison, high-energy collision-induced dissociation data can be recorded on an Applied Biosystems (Foster City, Calif.) 4700 Proteomics Analyzer using 2-keV fragmentation energy with air as the collision gas. Low energy CID can be performed on a ThermoFinnigan LCQ Deca XP (Waltham, Mass.) using an atmospheric pressure MALDI ionization source.

In another illustrative embodiment, a variation of the device 50 shown in FIG. 6 is described, and represents another tandem time of flight instrument, wherein precursor ions are generated by electrospray rather than MALDI. It is appreciated that electrospray may be used to analyze larger protein samples, where MALDI may be used to analyze smaller peptide samples. Illustratively, electrospray may be used to generate multiple charges on a protein sample for analysis. Fragmentation of the protein sample carrying multiple charges using the devices, methods, and apparatus described herein directly produces charged fragment ions.

In another aspect, the high molecular weight compounds analyzed are peptides that include a single highly basic residue. It is appreciated that such peptides tend to produce either a or x ions when fragmented by photodissociation, including photodissociation at 157 nm. It is further appreciated that peptides having multiple basic sites, or those lacking a highly basic group may also yield both of these a and x ion series. In this latter case, it is appreciated that any difficulty in interpreting the results may, and is often, offset by the presence of v-x pairs. It is appreciated that v ions and w ions are produced by mechanistically similar processes. Therefore, spectra that tend to show high populations of v ions, also tend to show high populations of w ions. Similarly, spectra that tend to show high populations of w ions, also tend to show high populations of v ions. For example, proteins and peptides that include branched-chain alkyl side chain amino acids, such as isoleucine and leucine, tend to form both w and v ions from such side chains. With no corresponding pair observed for a fragments, the presence of v-x pairs may help to differentiate N- and C-terminal fragment ions.

In another aspect, methods described herein that include photodissociation using 157 nm light with a photon energy of 7.9 eV may induce unusual fragmentations between $C_\alpha$ and the backbone carbonyl-carbon of singly-charged peptide ions. Specific cleavage to form x and v type fragment ions has not been previously reported, and may result from excitation of a dissociative electronic state by the 157 nm photon. The specificity is not normally observed in vibrationally excited peptide ions nor with electron capture dissociation, which imparts a similar energy to the analyte in a discrete process. It is believed that the fragmentation induced by VUV may be occurring without electronic to vibrational relaxation. Thus, the embodiments described herein are suited for the investigation, analysis, and/or sequencing of relatively large or high molecular weight molecules. The relative similarity of the intensities of different photofragment ion peaks suggests that chromophores associated with this VUV excitation process are present all along the peptide backbone.

The specificity and predictability of 157 nm photodissociation of peptides is different from the results obtained from collision induced dissociation and post-source decay fragmentation of the same molecules. While the latter methods involving collision induced dissociation and post-source decay fragmentation usually produce a mixture of b and y fragments, both the coverage in each series and the types of fragments observed may vary widely. In some cases, the spectrum is dominated by the predicted fragments, while in others internal fragments or preferential fragmentation sites play an important role.

It is further understood that the methods and devices described herein may be used independently of other devices, components, or apparatus, or may be incorporated into any of a variety of conventional systems, including but not limited to conventional mass spectrometry systems and/or ion mobility spectrometer systems. In one embodiment, the devices and methods described herein may be added to such conventional mass spectrometry systems that do not have a molecular fragmentation component, or to such conventional mass spectrometry systems that do have a molecular fragmentation component as either a replacement component or as an additional optional molecular fragmentation component. Such mass spectrometry systems include those that cannot be adapted for use with ECD due to the presence of internal electrical fields. Such mass spectrometry devices also include those that use any of a variety of ionization techniques or components. In another embodiment, the devices and methods described herein may be added to conventional ion mobility systems, such as those described in U.S. Pat. No. 6,323,482, the disclosure of which is incorporated herein by reference.

It is appreciated that the methods and devices described herein are advantageously generalized for use with any one of a variety of other types of analysis instruments.

In another aspect, the sample to be analyzed using the methods, devices, and apparatus described herein includes one or more peptides and/or proteins. In aspects described herein that include peptides and/or proteins, such peptides and/or proteins may be digested with enzymes, including but not limited to trypsin, pepsin, V-8 protease, chymotrypsin, and the like. It is appreciated that selection of an enzyme for digesting peptides and/or proteins prior to analysis may be advantageously performed in order to decrease the average molecular weight of the components to be analyzed, and/or to increase the number of peptides that result from the enzymatic digest step that have one basic residue at either the N- or C-terminus.

Illustratively, in peptides generated by digesting proteins with the enzyme trypsin, the C-terminal residue will often be arginine or lysine. The presence of arginine at the C-terminus enhances the generation of x and v type fragments by 157 nm photodissociation, since arginine has the highest gas phase basicity of the amino acids. In contrast, because histidine has a higher gas phase basicity than lysine (A. G. Harrison, *Mass Spectrom. Rev.* 16, 201 (1997)), the charge will not always be sequestered at the C-terminus of lysine-containing tryptic peptides in peptide and peptide fragment ions that include both lysine and histidine. However, simple methods are available to increase the basicity of lysine residues, as described by R. L. Beardsley, J. P. Reilly, in *Anal. Chem.* 74, 1884 (2002); R. L. Beardsley, J. P. Reilly, J. Proteome Research, 2, 15 (2003), the disclosure of which is incorporated herein by reference. Such methods of increasing the basicity of lysine residues are contemplated in variations of the methods described herein. This increase in the basicity of lysine residues tends to improve the ionization efficiency of lysine-terminated peptides and increase the probability that most or all of the tryptic fragments resulting from complete digestion will produce C-terminal fragment ions. An alternative method for increasing the probability that most or all of these fragments are of the same type involves introducing a sulfonic acid group at the C-terminus; however, it is appreciated that this method may also reduce MALDI ionization efficiency. See, T. Keough, R. S. Youngquist, M. P. Lacey, *Proc. Natl. Acad. Sci. USA* 96, 7131 (1999).

In one illustrative variation, peptide digests that include a large number of C- and or N-terminal lysine residues may be further treated prior to analysis to convert the amino group of the lysine residue into a guanidino group. It is appreciated that such a conversion may increase the basicity of the lysine residues.

In another embodiment, methods and apparatus are described herein for sequencing peptides and/or proteins. In one aspect, trypsin digests, or other conventional enzymatic digests of peptides or proteins used for subsequent sequencing experiments form part of the methods. Enzymatic digests of such peptides and/or proteins are analyzed using mass spectrometric protein identification procedures, where these procedures include the methods and/or fragmentation devices described herein. In another aspect, the method includes a device or component capable of generating laser light at 157 nm for photodissociation of the peptides and/or proteins found in enzymatic digest, such as trypsin digests, and the like. The methods described herein are suitable for de novo peptide sequencing, allowing the direct interpretation of the fragmentation spectrum generated by the apparatus described herein. Such peptide sequences directly derived from mass spectrometric data identification are useful when appropriate database standards do not exist or contain database errors, or in cases where the peptide being analyzed has been mutated or post-translationally modified.

In another embodiment, the methods, devices, and apparatus described herein include the analysis of large and/or high molecular weight compounds. Illustrative large and/or high molecular weight compounds include, but are not limited to, peptides, proteins, carbohydrates, glycopeptides, glycoproteins, nucleic acids, synthetic polymers, and the like. In aspects of this embodiment, the methods, devices, and apparatus described herein use a source of laser light that has a predetermined wavelength for fragmentation of the compound or molecule to be analyzed. The predetermined wavelength is illustratively selective or specific for a bond type present in the molecule to be analyzed. It is appreciated that fragmentation methods described herein may be based on selecting the predetermined wavelength that corresponds to a bond type that is present in large numbers in the molecule to be analyzed. Thus, diverse fragments are generated allowing the structure or sequence of the molecule to be determined. In another illustrative aspect, the molecule to be analyzed is a peptide or protein, and the predetermined wavelength is selective or specific for a backbone amide bond. In other aspects of this embodiment, the methods, devices, and apparatus described herein use a source of laser light that has a predetermined energy that is sufficient for selectively or specifically breaking or cleaving the bond type present in the molecule to be analyzed. In another illustrative aspect, the molecule to be analyzed is a peptide or protein, and the predetermined energy is sufficient to selectively or specifically break or cleave a backbone amide bond.

In another embodiment, any of a variety of methods for producing molecular ions are included prior to fragmentation using the methods, devices, and apparatus described herein. Any suitable method for forming precursor ions, including but not limited to matrix assisted laser desorption/ionization (MALDI), electrospray (ES), sonic spray, electro-sonic spray, fast atom bombardment, and the like are contemplated. It is appreciated that depending on the molecules or compounds analyzed, these ion sources may produce singly charged ions, or multiply charged ions in some cases.

In another embodiment, any of a variety of mass analyzers are contemplated for use with the methods, devices, and apparatus described herein. Both precursor ions and photofragment ions can be isolated and identified using different types of mass analyzers, including but not limited to linear time of flight (LTOF), time of flight-time of flight (TOF-TOF), reflectron time of flight, linear ion trap-time of flight (LIT-TOF), triple-quadrupole, magnetic sector, quadrupole time-of-flight (Q-TOF), Fourier transform ion cyclotron resonance, linear, and 3D ion traps. The choice of the particular mass analyzers is made during routine optimization of the methods, devices, and apparatus described herein, with regard to sample compatibility, sensitivity, resolution, and other routinely optimized parameters. The ion photodissociation method is compatible with any of these mass analyzers. Some of these instruments have the capability of storing ions or performing higher order $MS^n$ experiments, which capabilities facilitate photofragmentation studies.

Following are illustrative exemplified embodiments of the invention described herein. These following examples are intended to illustrate various embodiments of the invention, and are not intended and should not be interpreted to limit the invention in any way. For example, the exemplified embodiments described herein were performed on a homebuilt MALDI tandem time-of-flight instrument. Nevertheless, it is to be understood that these exemplified embodiments as well as the other illustrative embodiments of the invention described herein are equally applicable to the full range of other homebuilt and/or commercially available mass spectrometers in contemplated variations of the invention.

EXAMPLES

Unless otherwise indicated, protein digest mixtures were analyzed without separation. Analysis of the protein digest mixtures was made using an instrument similar to those that employ collision cells, except that the ion fragmentation was induced by VUV laser light. Ions generated by MALDI were accelerated and separated in a short linear flight tube. During that time, post-source decay (PSD) ions were formed by unimolecular dissociation and continued to travel with the precursor ion. At the end of this first stage, a particular ion and its fragments were selected by an ion gate and then irradiated with a synchronized pulse of approximately 1 mJ of 157 nm (7.9 eV photon energy) light generated from an $F_2$ laser. The precursor ion and its fragments were reaccelerated into the second stage, a reflectron time-of-flight mass analyzer, where they were separated and detected with isotopic resolution obtained for both the parent and fragment ions. The $F_2$ laser was operated on alternating MALDI shots, and post-source decay fragments were distinguished from those generated by photodissociation. One illustrative matrix, 2,5-dihydroxybenzoic acid (DHB), was used as the matrix for the photodissociation experiments in order to minimize the production of post-source decay fragments. Another illustrative matrix, α-cyano-4-hydroxycinnamic acid (CHCA), was used to deliberately generate PSD fragments. It is appreciated that this matrix also tends to maximize the overall number of ions generated. Results for three peptide ions having basic groups at either their N-termini or their C-termini are presented.

Example 1

MALDI Mass Spectra of SEQ ID NO: 1, Angiotensin II (DRVYIHPF)

Figure 1:
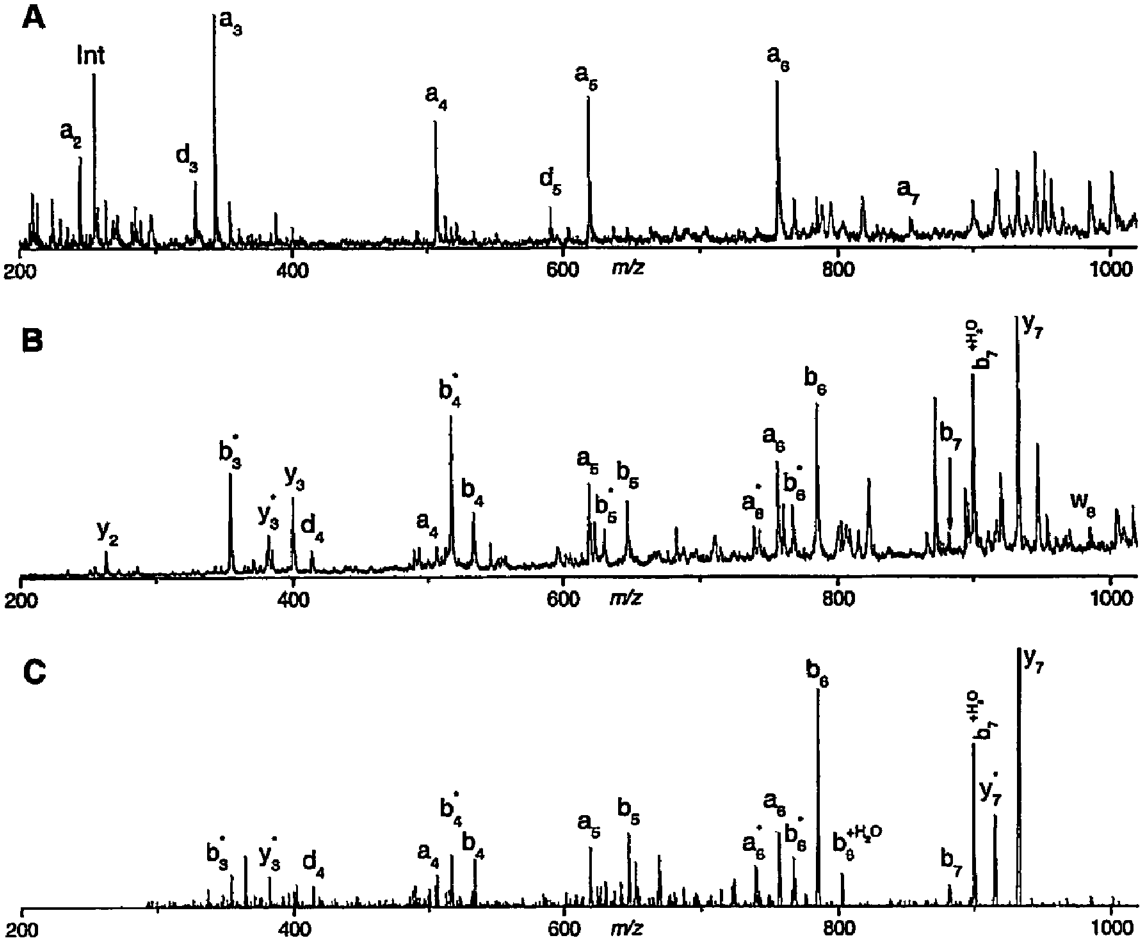
FIG. 1 shows MALDI mass spectra of SEQ ID NO: 1, Angiotensin II (DRVYIHPF) (A) 157 nm photodissociation with DHB matrix (B) Post-source decay using CHCA matrix (C) AP MALDI collision induced dissociation. Fragments labeled with * involve loss of $NH_3$.

The mass spectrum of the photofragments produced when singly-charged Angiotensin II ions were irradiated with 157 nm light was dominated by a series of a-type ions extending from $a_2$ to $a_7$ (FIG. 1A). These a ions were produced by the dissociation of α-carbon-carbonyl carbon bonds with the charge remaining on the N-terminal fragment. It is believed that the $a_7$ ion was lower in intensity than the other a series ions due to the adjacent proline. The peak labeled Int was interpreted as resulting from two a-type cleavages. The post-source decay spectrum of Angiotensin II recorded on the same instrument (but with the fragmentation laser not triggered) is shown in FIG. 1B. A collection of primarily a, b, and y fragments, different from the spectrum generated by photodissociation, were observed. None of the fragment series in FIG. 1B was complete, and the intensity of the peaks within each series varied widely. As expected, the CID data shown in FIG. 1C were qualitatively similar to the PSD results

Example 2

MALDI Mass Spectra of SEQ ID NO: 2, a Hemoglobin Tryptic Peptide (LLVVYPWTQR)

Figure 2:
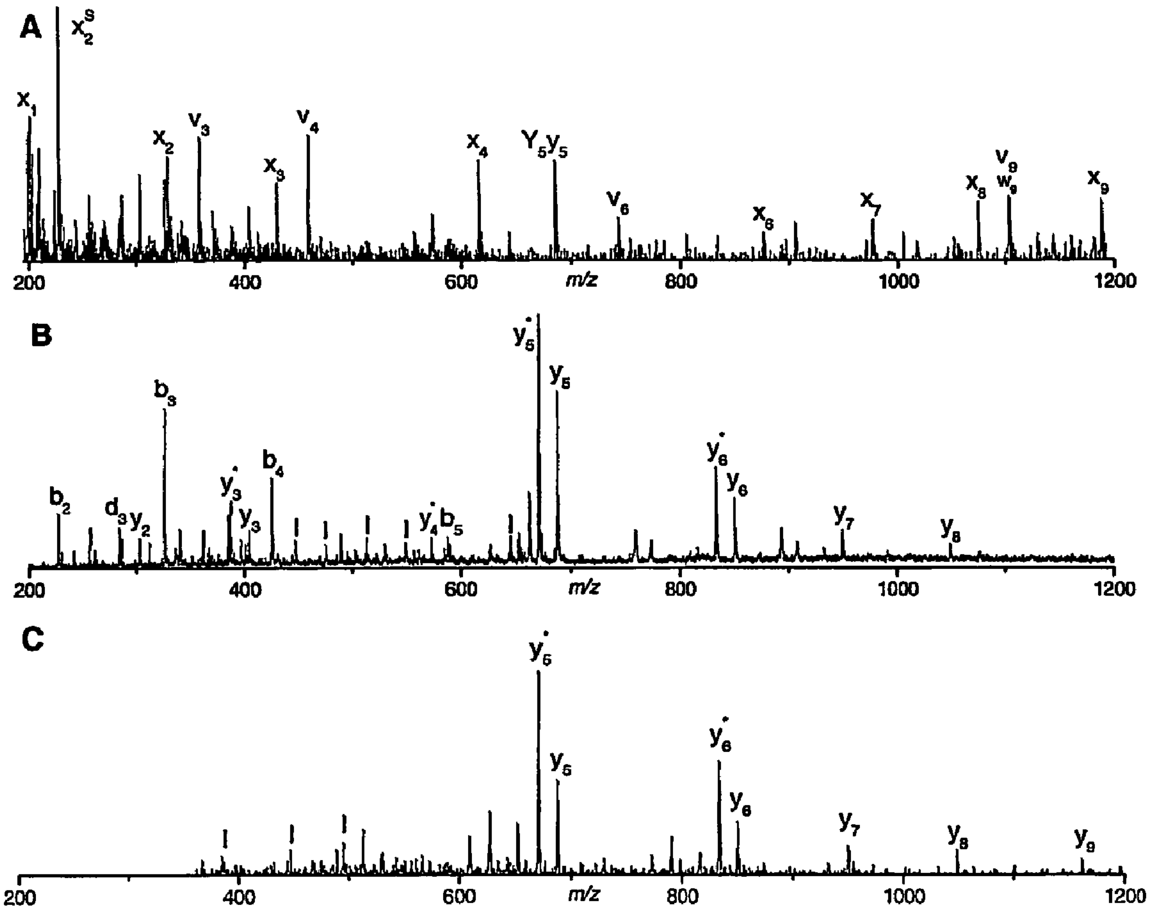
FIG. 2 shows MALDI mass spectra of SEQ ID NO: 2, a Hemoglobin tryptic peptide (LLVVYPWTQR) (A) 157 nm photodissociation using DHB as matrix (B) Post-source decay using CHCA matrix. (C) AP MALDI collision-induced dissociation. Peaks labeled I represent internal fragmentation.

The 157 nm photodissociation mass spectrum of a hemoglobin tryptic peptide is shown in FIG. 2A. It is believed that because of the basic arginine residue at the C-terminus, this spectrum was dominated by x and v ions. The x ions correspond to cleavage of the same α-carbon-carbonyl carbon backbone bond that breaks to form an a ion except that the charge remained on the C-terminal fragment. An x ion series extending from $x_1$ to $x_9$ , was observed, with only $x_5$ missing presumably due to the presence of proline. The v ions are high-energy C-terminal fragments that may have been formed from an x radical ion through loss of CO and an amino acid side chain, as described by R. S. Johnson, S. A. Martin, K. Biemann, in *Int. J. Mass Spectrom. Ion Processes* 86:137 (1988). It is believed that the concomitant appearance of both x and v type ions suggests that 157 nm photodissociation of peptides involves a radical cleavage process. The $w_9$ ion observed in this spectrum represents a partial leucine side chain loss. The pair of peaks labeled $y_5$ and $Y_5$ represent a fragmentation of the N-terminal side of proline, and is believed to be unique. The $y_5$ ion peak is a standard y fragment formed by post-source decay, and is even observed with DHB as the matrix, because fragmentation on the N-terminal side of proline is highly favored, as described by D. F. Hunt, J. R. Yates, III, J. Shabanowitz, S. Winston, C. R. Hauer, in *Proc. Natl. Acad. Sci. USA* 83, 6233 (1986), and L. A. Breci, D. L. Tabb, J. R. Yates, III, V. H. Wysocki, in *Anal. Chem.* 75, 1963 (2003). The carbonyl carbon amide nitrogen bond is cleaved and two protons are transferred to the nitrogen during the formation of y ions. The Y ions involve the same backbone cleavage, but without proton transfer, resulting in a peak having a mass 2 daltons lower than the corresponding y ions. The $Y_5$ fragment was induced by 157 nm photodissociation; it is believed that a radical x precursor ion loses CO and hydrogen. In contrast with v ion formation, the loss of the side chain is prevented by the cyclic proline structure. The peak labeled $x_2^S$ in FIG. 2A was interpreted as an $x_2$ ion that also loses an arginine side chain. The PSD and CID spectra of this peptide (FIGS. 2B & 2C) both show typical fragmentation patterns containing a mixture of y, b, and internal fragment ions.

Example 3

MALDI Mass Spectra of SEQ ID NO: 3, the Peptide FSWGAEGQR

Figure 3:
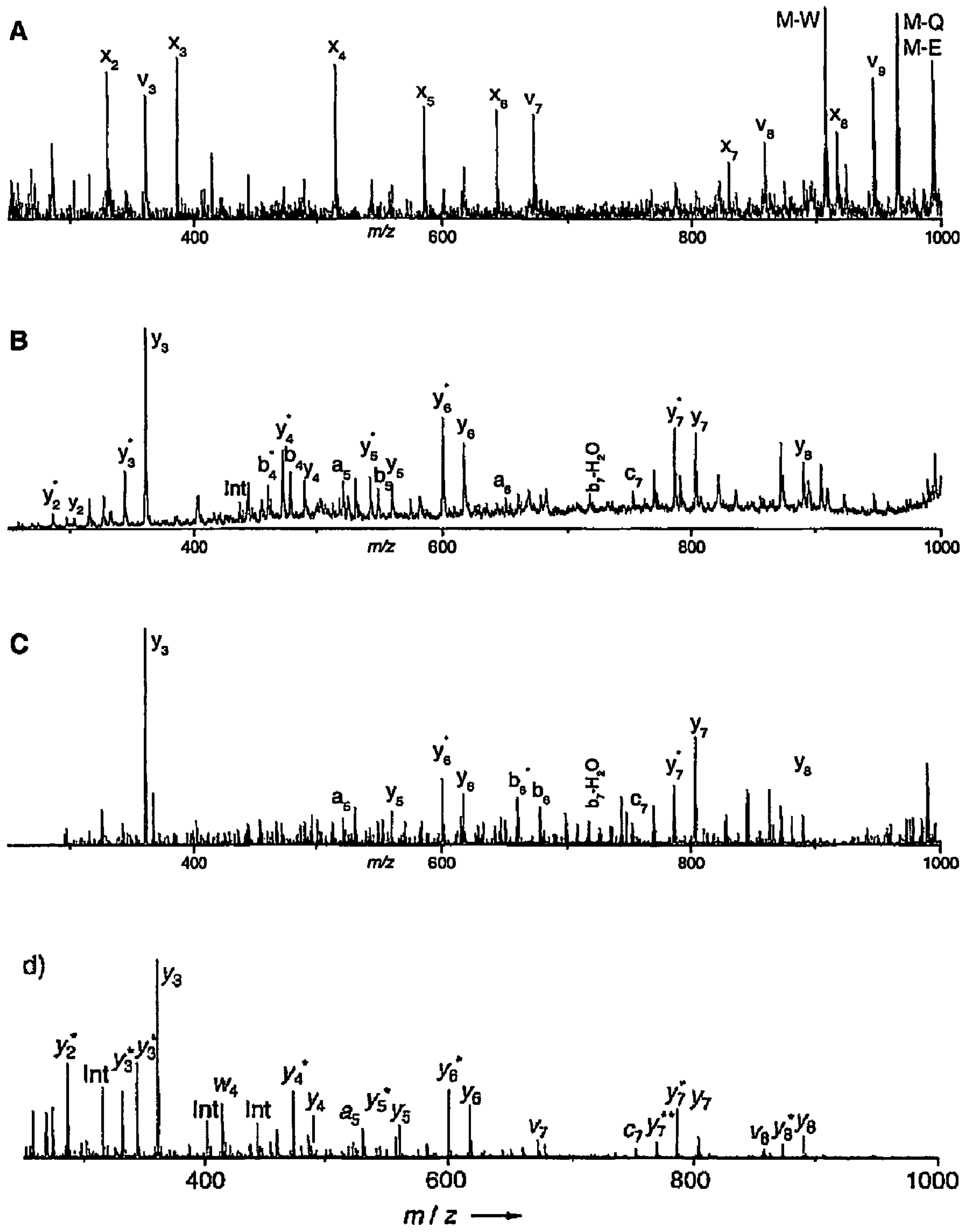
FIG. 3 shows MALDI mass spectra of SEQ ID NO: 3, the peptide FSWGAEGQR (A) 157 nm photodissociation using DHB as matrix (B) Post-source decay using CHCA matrix. (C) AP MALDI collision-induced dissociation, (D) 2-keV TOF-TOF collision-induced dissociation. The * and ** labels represent the loss of one and two $NH_3$ groups, respectively.

The mass spectrum of the photoproducts from the 157 nm dissociation of singly-charged SEQ ID NO: 3, FSWGAEGQR ions is shown in FIG. 3A. In contrast to Angiotensin II, this spectrum was dominated by x and v ions. The x ions correspond to cleavage of the same α-carbon-carbonyl carbon backbone bond that breaks to form an a ion except that the charge remained on the C-terminal fragment. The v ions are high-energy C-terminal fragments that are believed to originate from cleavage of the α-carbon-carbonyl carbon backbone bond followed by loss of CO and an amino acid side chain. It is believed that the concomitant appearance of both x and v type ions suggests that 157 nm photodissociation of peptides involves a radical cleavage process. Since the mass difference between $x_n$ and $v_{n+1}$ is constant, these ion pairs in the spectrum were readily identified. In addition to the x and v ions, peaks corresponding to the neutral loss of the side chains of glutamine, glutamic acid, and tryptophan from the intact precursor also appeared between 900 and 1000 daltons, as shown in FIG. 3A. Neutral losses have also been reported with ECD, where protonated side chains are specifically fragmented. See, H. J. Cooper, R. R. Hudgins, K. Håkansson, A. G. Marshall, *J. Am. Soc. Mass Spectrom.* 13, 241 (2001). The post-source decay spectrum of the peptide SEQ ID NO: 3, FSWGAEGQR (FIG. 3B) contained nearly only the y and b ion series, as well as a large number of y-$NH_3$ fragments.

Considerable peak intensity variation was again observed. Many peaks corresponding to internal fragments (left unlabeled for clarity), in which the backbone was cleaved twice, were also observed from this peptide. The CID spectrum obtained by atmospheric pressure MALDI, shown in FIG. C, is similar to that obtained by PSD.

Example 4

MALDI Mass Spectra of the Peptides SEQ ID NO: 4, ALELFR, SEQ ID NO: 5, LFEELAR, SEQ ID NO: 6, IENHEGVR, and SEQ ID NO: 7, EGVNDNEEGFFSAR.

Figure 4:
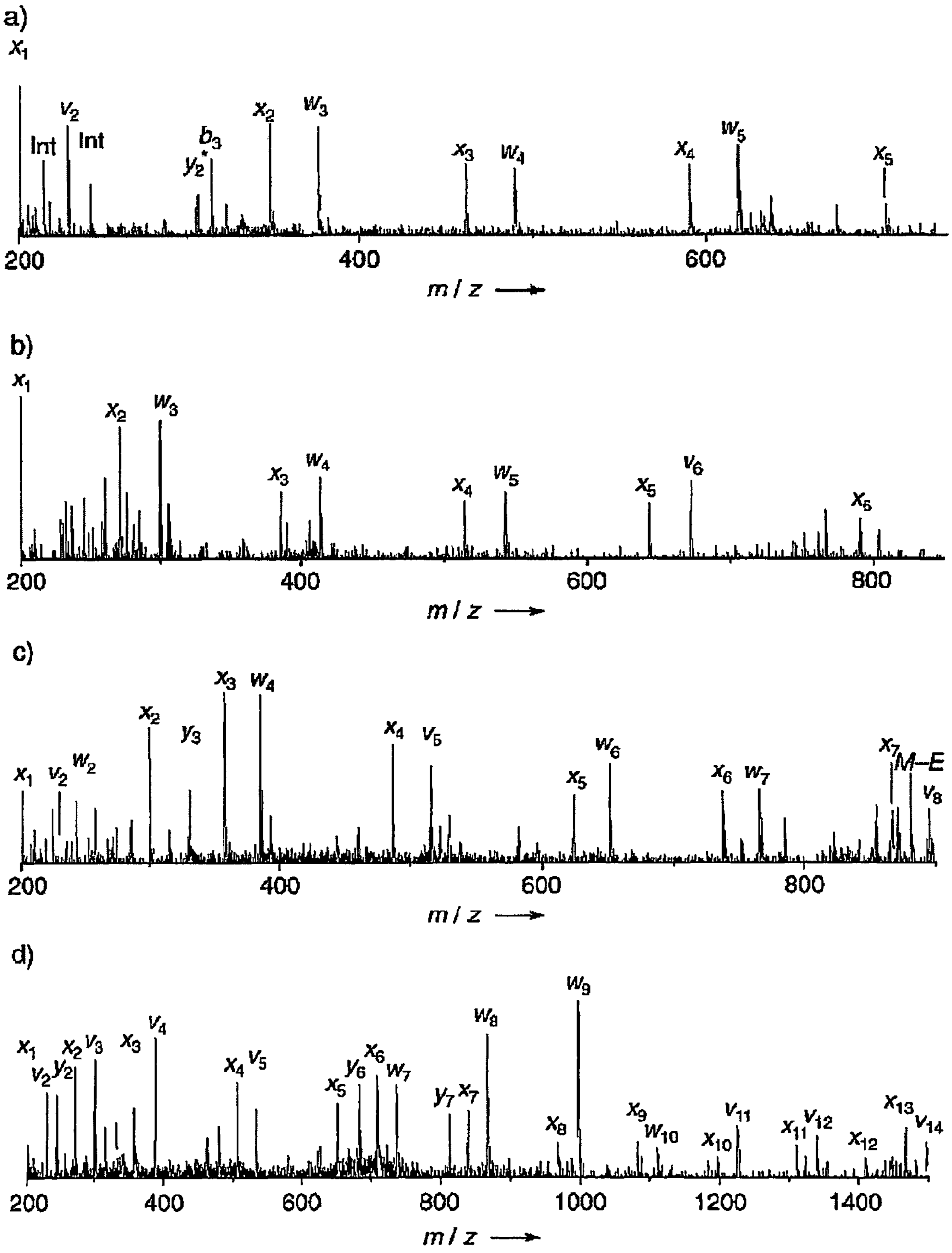
FIG. 4 shows four typical mass spectra of peptides with basic residues (arginine) at their C-termini that were fragmented using 157-nm photodissociation. Each spectrum is dominated by x, v, and w fragments. The w fragments were observed at leucine residues, rendering them distinguishable from isoleucine. It is believed that the b- and y-type ions appearing in these spectra generally correspond to intense PSD fragments that were not completely eliminated with background subtraction. A) SEQ ID NO: 4, ALELFR; B) SEQ ID NO: 5, LFEELAR; C) SEQ ID NO: 6, IENHEGVR; D) SEQ ID NO: 7, EGVNDNEEGFFSAR. Peaks labeled Int are internal fragments. The * label represents the loss of one NH3 group.

The mass spectrum of the photoproducts from the 157 nm dissociation of singly-charged SEQ ID NO: 4, ALELFR, SEQ ID NO: 5, LFEELAR, SEQ ID NO: 6, IENHEGVR, and SEQ ID NO: 7, EGVNDNEEGFFSAR ions are shown in FIG. 4. These spectra were generated following the general procedure described in Example 1, where A) is SEQ ID NO: 4 ALELFR, B) is SEQ ID NO: 5, LFEELAR, C) is SEQ ID NO: 6, IENHEGVR, and D) is SEQ ID NO: 7, EGVNDNEEGFFSAR.

What is claimed is:

1. A device for fragmenting a peptide ion or protein ion substantially at one or more of the α-carbon-carbonyl carbon bonds present in the peptide ion or protein ion, the device comprising:

a first component capable of forming the peptide ion or protein ion from a sample, a second component which is different from the first component comprising a source of vacuum ultraviolet radiation adapted to deliver light at an energy sufficient to break at least one of the one or more α-carbon-carbonyl carbon bonds and produce one or more fragments of the peptide ion or protein ion, and a third component comprising a first mass analyzer, where the mass analyzer is operably connected to receive the one or more fragments of the peptide ion or protein ion.

2. The device of claim 1 wherein the vacuum ultraviolet radiation has a wavelength of about 157 nm.

3. The device of claim 1 wherein the source of vacuum ultraviolet radiation is a laser.

4. The device of claim 1 wherein the component capable of forming the peptide or protein ion from a sample is an electrospray device.

5. The device of claim 1 wherein the device further includes a fourth component comprising a second mass analyzer.

6. The device of claim 1 wherein the first mass analyzer is a time of flight mass analyzer.

7. The device of claim 5 wherein the second mass analyzer is a time of flight mass analyzer.

8. The device of claim 5 further comprising an ion trap adapted for trapping the peptide ion or protein ion prior to fragmentation.

9. The device of claim 8 wherein the ion trap is coupled to the second mass analyzer.

10. The device of claim 1 further comprising a fifth component for measuring the mass/charge ratio of the one or more fragments.

* * * * *

UNITED STATES PATENT AND TRADEMARK OFFICE

CERTIFICATE OF CORRECTION

PATENT NO. : 7,618,806 B2
APPLICATION NO. : 10/578679
DATED : November 17, 2009
INVENTOR(S) : James P. Reilly It is certified that error appears in the above-identified patent and that said Letters Patent is hereby corrected as shown below:

In column 1, line 19-22, please replace the text “This invention was made in whole or in part with support from The National Institutes of Health through NIH Grant No. GM061336. The United States Government may have certain rights in this invention.” with the text -- This invention was made with government support under GM061336 awarded by National Institutes of Health. The U.S. Government has certain rights in the invention. --

Signed and Sealed this
Twenty-second Day of March, 2011

David J. Kappos
*Director of the United States Patent and Trademark Office*

SEQUENCE LISTING

```
<160> NUMBER OF SEQ ID NOS: 7

<210> SEQ ID NO 1
<211> LENGTH: 8
<212> TYPE: PRT
<213> ORGANISM: Homo sapiens

<400> SEQUENCE: 1

Asp Arg Val Tyr Ile His Pro Phe
1               5


<210> SEQ ID NO 2
<211> LENGTH: 10
<212> TYPE: PRT
<213> ORGANISM: Homo sapiens

<400> SEQUENCE: 2

Leu Leu Val Val Tyr Pro Trp Thr Gln Arg
1               5                   10


<210> SEQ ID NO 3
<211> LENGTH: 9
<212> TYPE: PRT
<213> ORGANISM: Artificial
<220> FEATURE:
<223> OTHER INFORMATION: Control peptide available from Sigma (St.
      Louis, MO, USA)

<400> SEQUENCE: 3

Phe Ser Trp Gly Ala Glu Gly Gln Arg
1               5


<210> SEQ ID NO 4
<211> LENGTH: 6
<212> TYPE: PRT
<213> ORGANISM: Equus caballus

<400> SEQUENCE: 4

Ala Leu Glu Leu Phe Arg
1               5


<210> SEQ ID NO 5
<211> LENGTH: 7
<212> TYPE: PRT
<213> ORGANISM: Oryctolagus cuniculus
```

-continued

```
<400> SEQUENCE: 5

Leu Phe Glu Glu Leu Ala Arg
1               5


<210> SEQ ID NO 6
<211> LENGTH: 8
<212> TYPE: PRT
<213> ORGANISM: Oryctolagus cuniculus

<400> SEQUENCE: 6

Ile Glu Asn His Glu Gly Val Arg
1               5


<210> SEQ ID NO 7
<211> LENGTH: 14
<212> TYPE: PRT
<213> ORGANISM: Homo sapiens

<400> SEQUENCE: 7

Glu Gly Val Asn Asp Asn Glu Glu Gly Phe Phe Ser Ala Arg
1               5                   10
```